(12) United States Patent
Graham et al.

(10) Patent No.: US 9,498,564 B2
(45) Date of Patent: Nov. 22, 2016

(54) SHED-FORMING DEVICE FOR A WEAVING MACHINE

(71) Applicants: James Anthony Graham, Weardale-Durham (GB); Matthew Theobald, Consett-Durham (GB); Bram Vanderjeugt, Ieper (BE); Frederik de Medts, Ooigem (BE)

(72) Inventors: James Anthony Graham, Weardale-Durham (GB); Matthew Theobald, Consett-Durham (GB); Bram Vanderjeugt, Ieper (BE); Frederik de Medts, Ooigem (BE)

(73) Assignee: NV MICHEL VAN DE WIELE, Kortrijk/Marke (BE)

(*) Notice: Subject to any disclaimer, the term of this patent is extended or adjusted under 35 U.S.C. 154(b) by 0 days.

(21) Appl. No.: 14/740,777

(22) Filed: Jun. 16, 2015

(65) Prior Publication Data

US 2015/0275405 A1    Oct. 1, 2015

Related U.S. Application Data

(62) Division of application No. 13/996,962, filed as application No. PCT/EP2011/006456 on Dec. 21, 2011, now Pat. No. 9,091,001.

(30) Foreign Application Priority Data

Dec. 21, 2010  (BE) .................................. 2010/0748

(51) Int. Cl.
| | |
|---|---|
| *D03C 3/24* | (2006.01) |
| *D03C 3/00* | (2006.01) |
| *A61M 1/00* | (2006.01) |
| *D03C 3/20* | (2006.01) |
| *D03C 1/00* | (2006.01) |

(Continued)

(52) U.S. Cl.
CPC ............ *A61M 1/0058* (2013.01); *D03C 1/005* (2013.01); *D03C 3/00* (2013.01); *D03C 3/20* (2013.01); *D03C 13/00* (2013.01); *A61M 3/0283* (2013.01); *A61M 2205/33* (2013.01); *A61M 2205/3372* (2013.01); *A61M 2205/366* (2013.01)

(58) Field of Classification Search
CPC .......... D03C 3/20; D03C 3/24; D03C 13/00; D03C 3/00
See application file for complete search history.

(56) References Cited

U.S. PATENT DOCUMENTS

| | | | | | |
|---|---|---|---|---|---|
| 5,373,871 | A | * | 12/1994 | Speich ..................... | D03C 3/20 139/455 |
| 5,666,999 | A | * | 9/1997 | Dewispelaere .......... | D03C 3/20 139/455 |
| 5,782,272 | A | * | 7/1998 | Dewispelaere .......... | D03C 3/20 139/455 |

(Continued)

FOREIGN PATENT DOCUMENTS

| | | |
|---|---|---|
| EP | 0529025 A1 | 3/1993 |
| WO | WO9216680 A1 | 10/1992 |
| WO | WO2012084213 A3 | 9/2013 |

*Primary Examiner* — Bobby Muromoto, Jr.
(74) *Attorney, Agent, or Firm* — Symbus Law Group, LLC; Clifford D. Hyra

(57) ABSTRACT

A shed-forming device has elastically deformable selection elements (1) (28*a*)-(28*f*) which can be placed in an undeformed position or in a deformed position, electromagnetic selectors (2) which can be actuated in order to place or keep each selection element (1) in successive weaving cycles in one of said positions, and presenting means (3) in order to mechanically deform selection elements (1) in the direction of a selector (2) in each weaving cycle into a presenting position in which they are kept at a distance from the selector (2) by a stop (4), and also relates to a method for positioning selection elements of a shed-forming device in this manner.

5 Claims, 9 Drawing Sheets

(51) Int. Cl.
*D03C 13/00* (2006.01)
*A61M 3/02* (2006.01)

(56) References Cited

U.S. PATENT DOCUMENTS 5,794,665 A * 8/1998 Keim ................. D03C 3/00
139/455

5,813,441 A * 9/1998 Dewispelaere .......... D03C 3/24
139/455
5,839,481 A * 11/1998 Bassi ..................... D03C 3/24
139/455
6,478,055 B1 * 11/2002 Dewispelaere .......... D03C 3/24
139/455
8,720,492 B2 * 5/2014 Vanderjeugt ............ D03C 3/24
139/455

* cited by examiner

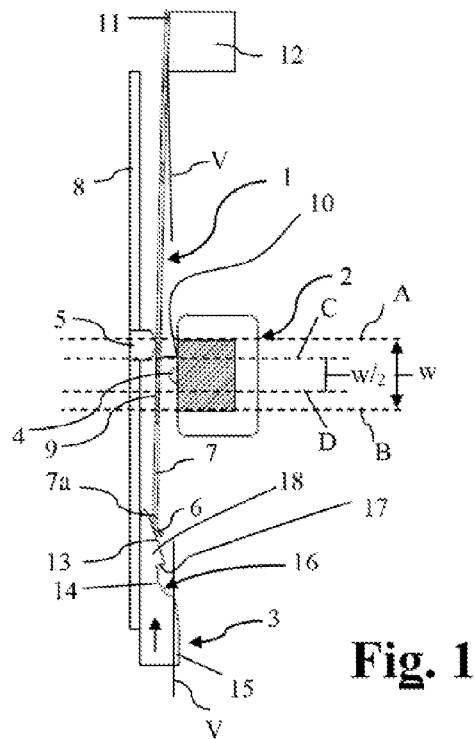
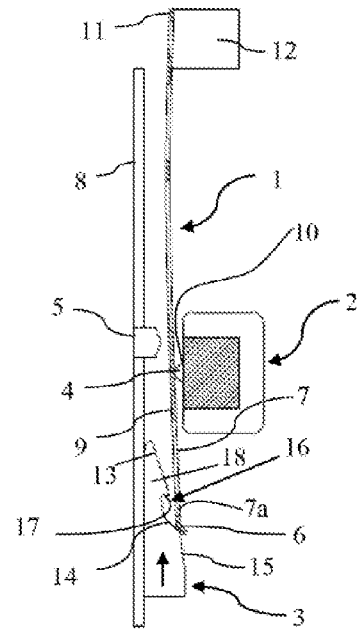
Fig. 1
Fig. 2
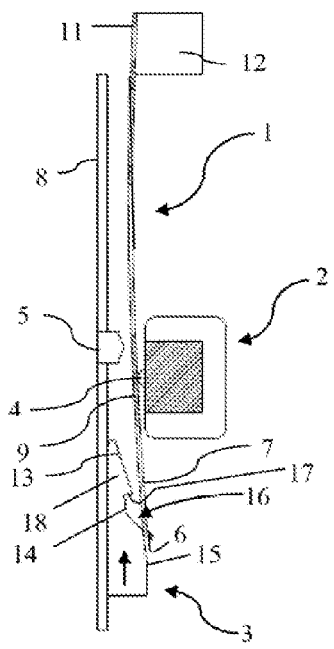
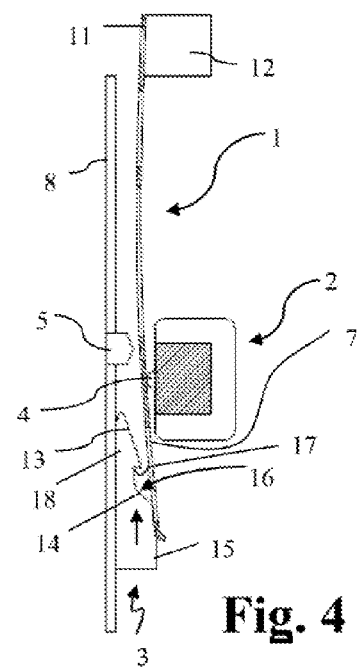
Fig. 3
Fig. 4

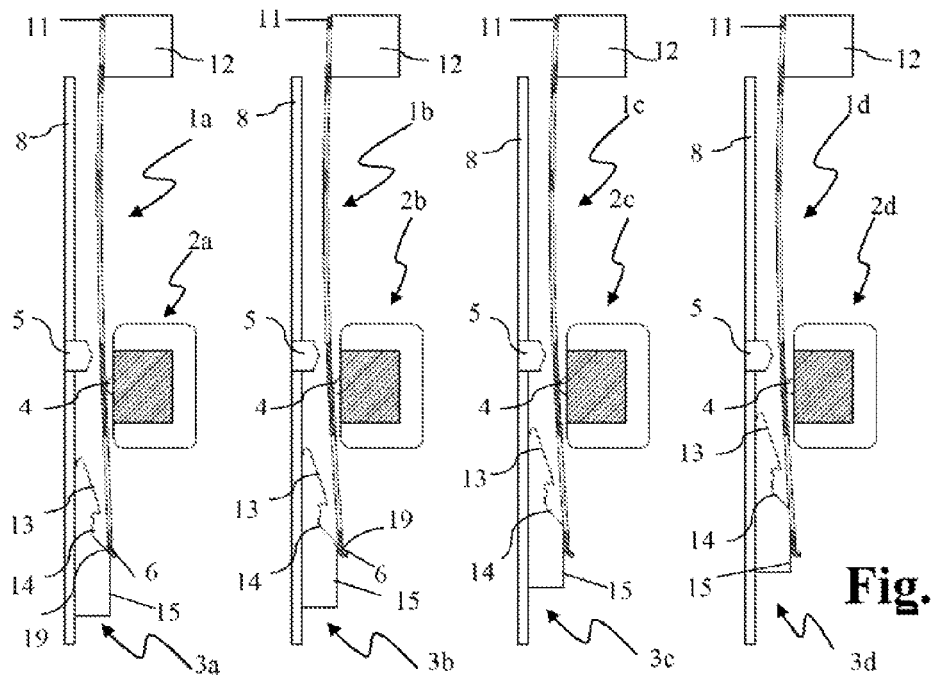
Fig. 15
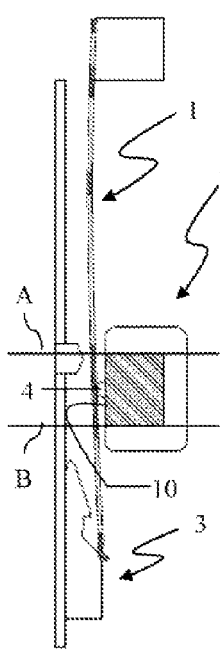
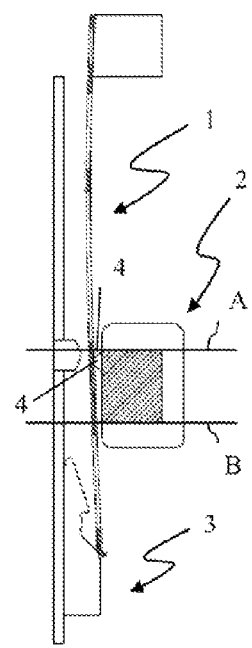
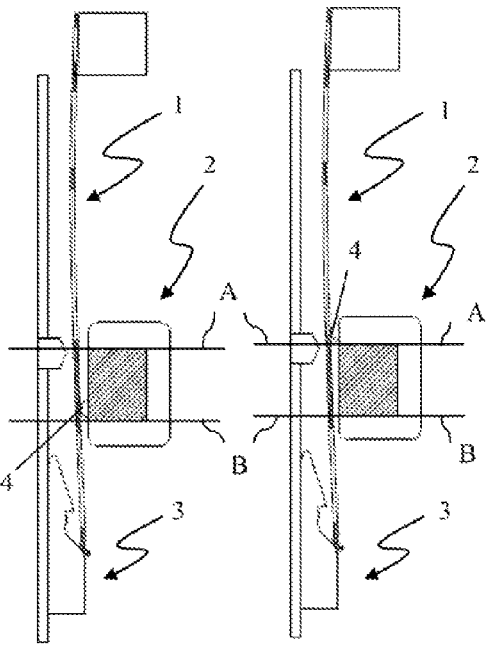
Fig. 16   Fig. 17   Fig. 18   Fig. 19

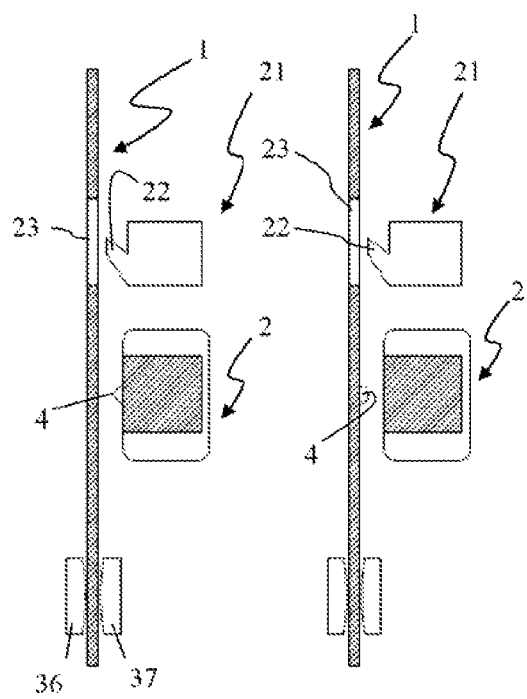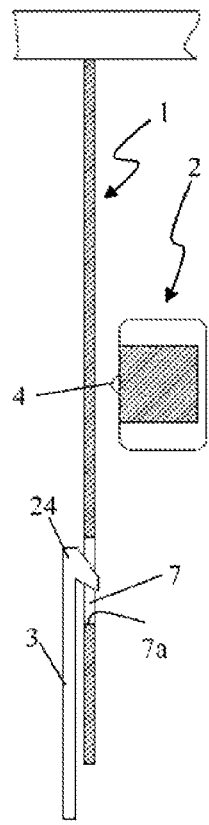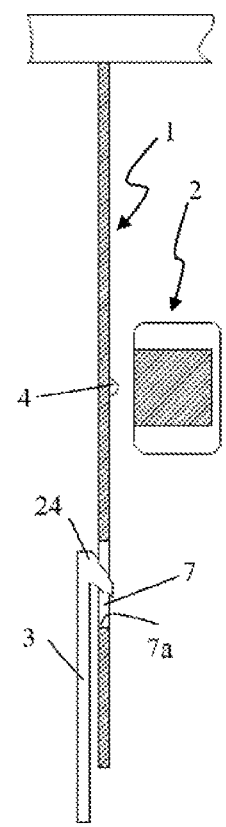
Fig. 20    Fig. 21    Fig. 22    Fig. 23

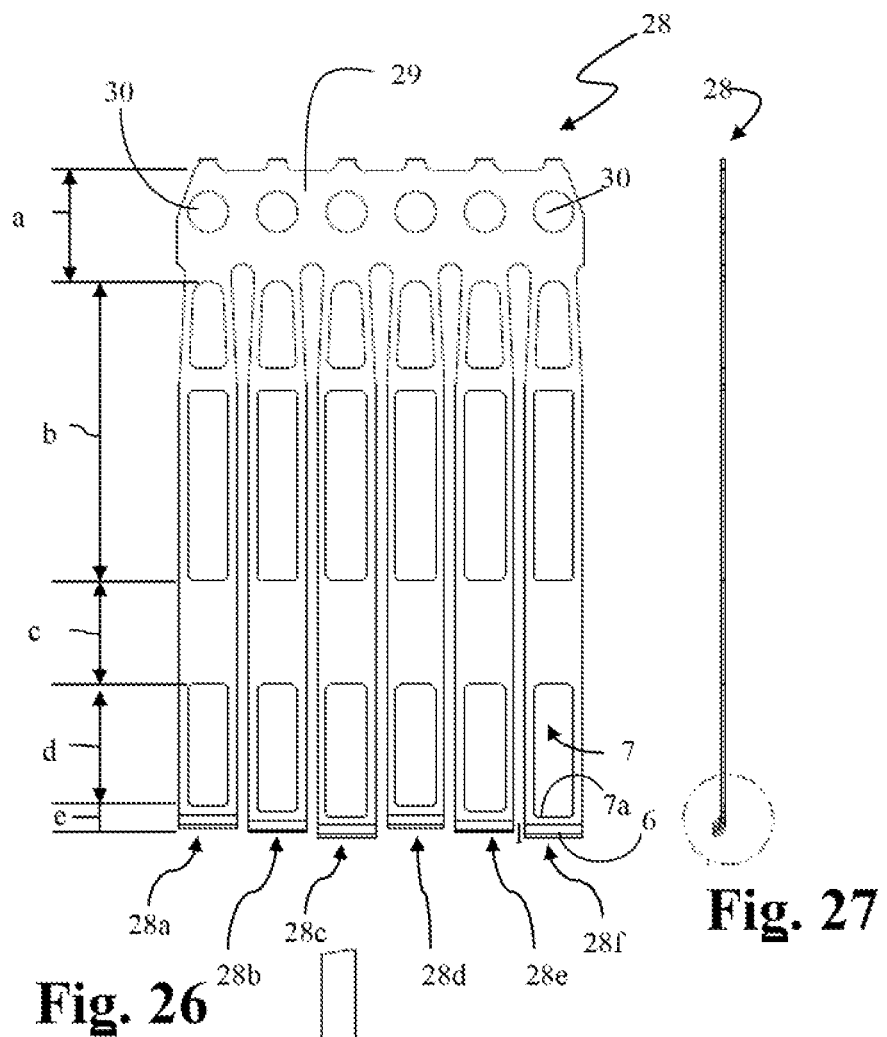
Fig. 26
Fig. 27
Fig. 28

SHED-FORMING DEVICE FOR A WEAVING MACHINE

This application is a divisional of Ser. No. 13/966,962 filed Jun. 21, 2013, which is a National Stage Entry of PCT/EP11/006456 filed Dec. 21, 2011 which claims priority to Belgian Application No. 2010/0748, filed Dec. 21, 2010, all of which are incorporated by reference in their entirety.

FIELD OF THE INVENTION

The present invention relates to a shed-forming device for a weaving machine comprising a number of elastically deformable selection elements, it being possible to optionally place each selection element in an undeformed position or in a deformed position in order to determine the position of at least one warp thread, a number of electromagnetic selectors which can be actuated in order to place or keep each selection element in successive weaving cycles in one of said positions, so that the warp threads are positioned in accordance with a predetermined weaving pattern, and presenting means which are designed to exert a mechanical force on a number of undeformed selection elements in each weaving cycle, as a result of which said selection elements are deformed in the direction of an associated selector.

BACKGROUND

When weaving a fabric on a weaving machine, the warp threads are positioned with respect to the level at which a pick thread is introduced in each cycle during the successive weaving cycles. The positions of the warp threads in the successive weaving cycles are in this case determined in such a manner that the weaving process results in a fabric having a predetermined weaving pattern. This positioning of warp threads with respect to the pick introduction level on a weaving machine, referred to as the shed formation, is automatically realized by means of a shed-forming device.

With a known shed-forming device of the jacquard type, each warp thread to be positioned passes through a heddle eyelet of a heddle. At the bottom, each heddle is connected to a retracting spring which exerts a downwardly directed force on the heddle and, at the top, is connected, via a harness cord, to the end of a tackle cord of a tackle system, which end is situated at a higher level. The tackle system comprises two hooks which are displaceable in the vertical direction. The position of these cooperating hooks determines the height of the end of the tackle cord, and thus also of the heddle eyelet and the warp threads passing through the latter.

Each hook can be displaced in the vertical direction by a respective knife. These two knives are driven so as to move in a up and down moving manner in opposite phases with respect to one another. Each hook comprises an elastically deformable portion, referred to as a selection element, which can be brought in a non-selection position or a selection position by actuating an electromagnetic selector. In the selection position, the selection element engages in a fixed hook-shaped projection as a result of which the hook is kept at a fixed height and is thus not caught by its knife. If the selection element is in the non-selection position, it cannot engage in the hook-shaped projection and the hook is caught by a downwardly moving knife. By positioning the hooks in the successive weaving cycles in this manner, a warp thread can be brought into the required successive positions via the tackle cord and the heddle in order to produce a fabric with the desired weaving pattern.

There are also shed-forming devices which comprise a flexible strip which is arranged at a fixed height and can be deformed by an electromagnetic selector and can thus be positioned with respect to a hook. This type of selection elements can optionally be brought into a selection position in which an associated hook can be attached to the selection element and is retained at a fixed height, or can be brought into a non-selection position in which said hook is not retained by the selection element and caught by a knife.

The electromagnetic selectors comprise a solenoid consisting of a core of magnetisable material around which electrically conducting coils are wound and one or more poles. The unit usually has a plastic housing. When an electric current flows through the coils, a magnetic flux is generated so that a deforming magnetic force is exerted on an associated selection element via one or more force-exerting poles of the selector.

By actuating the selector in order to optionally magnetically influence and deform a selection element, the selection element may be brought into the desired selection position or non-selection position.

It is known to provide shed-forming devices with presenting means which push the undeformed selection elements in each weaving cycle slightly in the direction of their respective selector, so that the magnetically influenceable parts of said selection elements are brought closer to the force-exerting poles. This results in an airgap between the magnetically influenceable parts of the selection elements and the selector poles which is less wide, and consequently less electrical energy is required to deform the selection elements.

This results in a reduction in the energy consumption of the numerous selectors in the shed-forming device. This is the case, inter alia, with the shed-forming device according to EP 0 529 025, where the elastically deformable selection elements are pushed in the direction of the selector by a reciprocating knife.

In such a jacquard machine, the chain of cooperating components in a shed-forming device: heddle, retracting spring, harness cord, tackle, selector, hook and hook-guiding means, is present numerous times. All these components have geometric deviations which are the result of, for example, inaccuracies during production and/or not having been accurately positioned and/or having been subjected to mutually different actions of forces, and consequently, the positions of these components are not determined exactly and show relatively large differences between one another. This applies in particular for the position of the various selection elements when these have been deformed in the direction of the selector by the presenting means.

This results in the selection elements being presented in mutually very different positions with respect to the associated selector poles, as a consequence of which the widths of the airgaps between different selection elements and the associated selector poles differ greatly from one another. This inaccurate positioning leads to errors in the selection of selection elements, resulting in weaving errors and weaving machine down time. The reliability of these shed-forming devices thus leaves something to be desired. In order to increase this reliability, it is possible to generate a higher magnetic flux, but this in turn results in an increased energy consumption.

SUMMARY

It is an object of the present invention to remedy the abovementioned drawbacks by providing a very reliable and also energy-saving shed-forming device.

This object is achieved by providing a shed-forming device having the features indicated in the first paragraph of this description, in which, according to the present invention, the presenting means are designed to mechanically deform the selection elements until they reach a presenting position in which they are kept at a distance from an associated selector by a stop.

The presenting means according to the present invention may be configured as movable elements which exert a mechanical force on the fixedly secured selection elements while they move, but may also be configured as fixedly secured elements with the selection elements moving and striking against the fixedly secured presenting means, so that the fixed presenting means exert a deforming mechanical reaction force on the moving selection elements. An embodiment in which both the presenting means and the selection elements move and move with respect to one another can also be produced.

The selection elements are preferably configured as strips or thin bands of flexible material, and usually also comprise openings to give the selection elements an ideal flexibility and reaction time.

In the context of the present invention, a stop is any obstacle or detaining means, irrespective of its position, which is arranged in such a manner or connected to the selection element in such a manner that it can limit the freedom of movement of a selection element to such a degree that this selection element is kept at a well-defined distance from the selector. According to the present invention, a stop does therefore not necessarily have to be provided on the selection element or on the selector or in the vicinity of the selector poles. A stop may also form part of another part or of a separate part, irrespective of its position with respect to the selector poles. Detaining means which are connected to the selection element and retain it when it has reached a well-defined position with respect to the selector may also fulfil that role and can thus be regarded as a stop.

By presenting all selection elements in a presenting position which is only determined by the position of a stop, the position of the presented selection elements with respect to their respective selector poles is no longer influenced by the abovementioned said deviations in geometry, position and load of the different components of the device. Said positioning is consequently much more accurate, so that the selection elements are presented in an essentially identical position with respect to the associated selector poles. This results in airgaps for the different selection elements which are far less different from one another, thus rendering said shed-forming device much more reliable than the known shed-forming devices which provide a presentation of elastic selection elements. In other words, this greatly increases the certainty that the applied electrical power is sufficient to place the selection element in the desired position compared to the known shed-forming devices.

For the sake of clarity, it should be stressed here that the electromagnetic selector can already be actuated before the presentation of the selection elements has finished. This is due to the fact that it is important for the presentation that the selection elements ultimately end up in a position in which it is quite certain that the applied electrical power is sufficient to place or keep the selection elements in the desired position. In this case, the time at which the selector coil is energized is completely immaterial.

The presentation of the selection elements leads to a reduction of the energy consumption, as the width of the airgap is made smaller. Thus, by placing each stop in such a manner that the magnetically influenceable parts of the selection elements placed in the presenting position are at a very small distance from the selector poles, a shed-forming device is produced which is also very energy-saving.

If more selection elements are presented by the same pushing means which imposes a similar movement trajectory on these selection elements or by different pushing means which move according to an identical movement trajectory, then the selection elements, due to the above-mentioned deviations in shape and position, will not simultaneously come into contact with their stop, but at different points in time. This means that it has to be ensured that the movement trajectory is sufficiently long to push all selection elements against a respective stop. After all, the presentation movement has to be continued until eventually the last selection element also bears against a stop. This results in the selection elements which have come into contact with their stop sooner being pushed in the direction of their selector with a greater force than is required to bring the selection element into contact with its stop, as a consequence of which they are deformed further. In the present patent application, this is referred to by the term 'overpresenting' or 'overpresentation'.

In a first, particularly preferred embodiment, the shed-forming device according to the present invention comprises at least one reciprocating knife and a number of shed-forming elements which can be caught by a knife in successive weaving cycles in order to change the position of one or more warp threads, while each selection element is arranged at a fixed height and is designed to retain an associated shed-forming element at a fixed height, and while each selection element is designed to, in the one position, retain the associated shed-forming element at a fixed height and, in the other position, not to retain said shed-forming element and allow it to move along with a knife.

Such a shed-forming device uses, for example, selection elements which are configured as thin elastically deformable bands or strips made from a material which is magnetically influenceable, and are fixedly secured at one end and extend next to an electromagnetic selector from said end. By optionally energizing the associated selector, each selection element can be brought to one or the other position in order to retain an associated shed-forming element (such as a hook) optionally at a fixed height.

The selection elements are, for example, provided with hook-engagement means which can cooperate in the selection position with complementary hook-engagement means on the shed-forming element, so that the shed-forming element is retained at a fixed height. The selection elements may, for example, be provided with a hook-engagement opening into which a hook-shaped portion or a projection of a shed-forming element can hook. Conversely, the shed-forming elements may also comprise an opening, while the selection elements are provided with a hook-shaped portion or a projection.

In a second, particularly preferred embodiment, said shed-forming device comprises at least one reciprocating knife, while each selection element forms part of a shed-forming element which can be caught by a knife in successive weaving cycles in order to change the position of one or more warp threads, and while each shed-forming element is designed to be retained at a fixed height in the one position of the selection element and to be caught by a knife in the other position of the selection element.

Such a shed-forming device makes use, for example, of selection elements which are configured as thin, elastically deformable bands or strips made from a magnetically influenceable material, and with one end are fixedly secured to or form part of a reciprocating shed-forming element, while the other end is free. The selection element can thus be an elastically deformable portion of a shed-forming element.

During the movements of the shed-forming element which are imposed by the knife, the selection element reaches a position in each weaving cycle in which it extends next to an electromagnetic selector. In this position, the selection element can be brought from one position to the other position by actuating the associated selector. At a fixed height, hook-engagement means are, for example, provided into which selection elements which have been brought into the one position engage so that the shed-forming elements connected thereto are retained at a fixed height. In the other position, the selection elements cannot engage into these hook-engagement means.

In the shed-forming device according to the present invention, the respective selectors are preferably provided with a stop having a contact area which faces an associated selection element, so that each selection element bears against the contact area of a stop of an associated selector when it is placed in the presenting position and is thus kept at a distance from a pole surface of said selector.

In this shed-forming device, it is also possible to provide the respective selection elements with a stop having a contact area facing the associated selector, so that each selection element, when it is placed in the presenting position, bears against an associated selector with the contact area of its stop and is thus kept at a distance from a pole surface of said selector.

The overpresentation of a selection element results in the selection element being deformed further in the direction of the selector than is required (i.e. further than is required to come into contact with its stop). In this case, the selection element is bent while it bears against the stop. The stop acts as a support and divides the selection element into two portions, as it were: the portion on which the force is exerted in order to deform the selection element in the direction of the selector and the other portion which, situated on the other side of the stop, is connected, for example, to a fixedly secured part or to a reciprocating shed-forming element. Exerting said force causes the selection element to assume a bent shape with the stop as support, and in order to reach said position, the portion on which the force is being exerted moves towards the selector poles, while the other portion moves away from the selector poles.

By overpresenting, the portion on which the force is exerted is thus moved towards a selector pole so that the intermediate airgap becomes narrower. The magnetic force which is exerted on the selection element in said spot will thus increase. In order to ensure that this overpresentation has virtually no effect on the total magnetic force which is exerted on the selection element via the selector poles, the stop is placed in such a manner that its contact area is situated in the space between the parallel transverse planes which delimit the zone of the force-exerting pole surfaces.

The contact area of the stop is then provided in the zone of the pole surfaces when the stop is provided on the selector, or is provided in the presenting position adjoining this zone if the stop is provided on the selection element. Consequently, overpresenting causes the portion of the selection element on which the force is exerted to come closer to a pole surface, while the other portion, on the other side of the stop, is taken further from a pole surface due to the bending of the selection element. The average airgap width or the air volume between the magnetically influenceable parts of the selection elements on the one hand and the associated selector poles on the other hand thus remains approximately similar, so that the total magnetic force as well only changes very little or not at all.

Preferably, each stop is placed in such a manner that its contact area is situated in a central part of said space, with said central part lying centrally between said transverse planes and being delimited by two parallel boundary surfaces having an intermediate distance which is half the intermediate distance between said transverse planes.

The magnetically influenceable parts of the selection element which are situated on either side of the stop opposite a pole surface can thus have approximately the same length. If the overpresentation causes a certain decrease in the air volume on one side of the stop, a virtually identical increase in air volume is produced on the other side of the stop. The total air volume between the magnetically influenceable parts of the selection elements on the one hand and the associated selector poles on the other hand thus changes very little, so that the influence of the overpresentation on the total magnetic force which is exerted on the selection elements is very limited.

In a preferred embodiment, the contact area of the stop is a substantially convex surface. As a result thereof, there is a minimal contact area between the selection element and the stop (if this is provided on the selector) or between the selector and the stop (if this is provided on the selection element) and making and breaking the contact as well as the further deformation of a selection element bearing against the stop, inter alia in the case of overpresentation, can be effected in a very smooth manner with a minimum of wear and loss of energy.

Said contact area can be completely or partly convex. Preferably, the surface is convex along the longitudinal direction of the selection element. A convex shape along a direction at right angles to this longitudinal direction enables good contact if the pole surface of the selector and the contact area of the selection element do not run perfectly parallel according to said perpendicular direction. In addition, the position of the contact is better defined, as a result of which the physical behaviour of the selection element is unambiguously determined, as the lengths between holding point and contact point, and between contact point and free end, are fixed. However, a convex shape along these two mutually perpendicular directions or according to one or more other directions is also possible. A surface which is completely or partly spherical is most advantageous.

In an ideal shed-forming device, the different selection elements are deformed until they just reach the stop during their presentation, so that no overpresentation is required. However, in practice, as has already been mentioned above, several selection elements will often be presented by pushing means which move along the same movement trajectory, and then, due to the abovementioned deviations in shape and position, the selection elements will not come into contact with their stop simultaneously, but one by one and at different points in time during this presentation. In order to ensure presentation of all selection elements against their respective stops during the movement trajectory of the pushing means, overpresentation is required.

Preferably, each selection element is connected at one end to a part of the shed-forming device, while the other end is free. In order to limit the energy required for the overpresentation and the additional friction and wear associated with overpresentation to a minimum and at the same time also increase the speed of response of the selection element, the selection element is preferably provided with a magnetically influenceable zone which, in the presenting position, substantially extends opposite the zone of the associated selector in which the pole surfaces extend, and with a flexible (elastically deformable) zone, whose stiffness is lower than the stiffness of the magnetically influenceable zone, and which is situated between the magnetically influenceable zone and the free end.

If the presenting means exert a mechanical force which acts on the selection element in the vicinity of its free end, the abovementioned flexible zone ensures that the additional deformation of the selection element during overpresentation requires very little energy. The very low stiffness of the flexible zone is achieved by one or more of the following measures: a reduced cross section of the material, the provision of recesses, holes and/or omission of material.

Preferably, each selection element comprises the following zones, from the one to the other end:

a. a stiff zone in the vicinity of the one end;
b. a first flexible zone which has a lower stiffness (resistance to bending) than the stiff zone, and the flexibility of which determines the speed of response of the selection element when the associated selector is actuated in order to bring the selection element in the deformed or the undeformed position;
c. a magnetically influenceable zone with a greater stiffness than the first flexible zone,
d. a second flexible zone which is situated beyond the magnetically influenceable zone and which has a lower stiffness than the magnetically influenceable zone, and the flexibility of which determines the amount of energy which is required in order to deform a selection element which bears against a stop further in the direction of the selector; and
e. an end zone at the free end, where an end part forms a contact area for the presenting means.

The cross section of the first flexible zone is substantially determined according to the desired speed of response and the maximum magnetic force which can be exerted on the selection element. The cross section of the magnetically influenceable zone is substantially determined by the maximum magnetic flux through the material, but the desired stiffness partly determines the ration between the thickness and the width of this cross section. The cross section of the second flexible zone is substantially determined such that the selection element in this zone has a very low stiffness, so that the overpresentation of selection elements requires very little energy. The contact area of the end part is preferably relatively large in order to limit wear of the contact areas of the selection elements and the presenting means.

With this shed-forming device, each selection element is at one end preferably connected to a part of the shed-forming device while the other end is free, with the presenting means and the selection element being movable with respect to one another along the longitudinal direction of the selection element, and with the presenting means comprising at least one first guide flank which is designed in such a manner that the free end of the selection element comes into contact with the guide flank during the movement and follows this guide flank during the further movement, so that the free end is pushed in a sideward direction and the selection element is deformed.

Using such a shed-forming device, the presentation of a large number of selection elements can be achieved in an effective manner. The deformation achieved by means of this guide flank is preferably sufficient to bring the selection element into the presenting position.

Preferably, the presenting means is secured to a part which can be driven to perform a reciprocating movement, while the selection element is attached to a fixed part of the shed-forming device at a fixed height. Thus, the presenting means may, for example, be connected to or form part of a knife or a shed-forming element, such as a hook. In this case, the device can be configured in such a manner that the guide flank of the presenting means strikes against the bottom free end of the fixedly secured selection element during the ascending movement. During the further ascending movement of the presenting means, the free end of the selection element slides over the guide flank which is moving upwards and the free end is gradually displaced sideways towards the selector. As a result thereof, the selection element is deformed in order to bring it into the presenting position. The material from which the selection element is made is preferably spring steel.

In a variant embodiment, the situation is reversed: here, the selection element is secured to a part which can be driven to perform a reciprocating movement, while the presenting element is attached to a fixed part of the shed-forming device at a fixed height. Thus, the selection element can, for example, be connected to or form part of a shed-forming element, such as a hook. The device can be configured in such a manner that the top free end of the flexible selection element strikes the guide flank of the fixedly secured presenting means during the upward movement. During the further upward movement of the selection element, the free end follows the guide flank, as a result of which it is gradually displaced sideways towards the selector. As a result thereof, the selection element is deformed in order to bring it into the presenting position.

Preferably, the shed-forming device is configured as having a presenting means which comprises a second guide flank which is designed in such a manner that, during the further movement beyond the first guide flank, the free end of the selection element comes into contact with said second guide flank and follows said second guide flank, so that the selection element is first pushed further towards the selector and is deformed further and then maintains virtually the same deformation during the further movement.

As mentioned above, the first guide flank ensures that the selection element is deformed into the presenting position or in the vicinity thereof. The second guide flank now has a first part which causes an additional deformation so that the selection element is guaranteed to be pushed against the stop, even with different positioning and/or with a different shape or dimensions. For a number of selection elements, this will result in overpresentation, as explained above.

Then, there has to be sufficient time to allow the selected shed-forming elements to engage with their hook-engagement means to retain them at a fixed height. To this end, the selection elements have to be kept in their deformed position for a short period of time during the further movement of the presenting means or during their own movement with respect to the presenting means.

In order to achieve this, the second guide flank comprises a second part which is designed in such a manner that the free end of the selection element comes into contact with this second part during the further movement beyond the first part, and follows this second part, so that, during the further movement, the selection element maintains virtually the same deformation which has been achieved before. This deformation to be maintained is preferably the deformation which has been achieved by the first part.

The first guide flank and the first and the second part of the second guide flank can be configured as an uninterrupted flank or may consist of two or three part flanks with intermediate breaks. The first part of the second guide flank may, for example, together with the first guide flank, form an uninterrupted flank while the second part of the second guide flank is configured as a separate flank. The separate second guide flank may also only comprise the first or the second part of the flank, with the other part being omitted.

If the second part of the second guide flank on the presenting means has a small incline with respect to the direction of movement (an incline which is smaller than the incline of the selection element at that location with respect to the direction of movement) or runs parallel to this direction of movement, then the selection element is deformed further during the further movement along this second part, as the contact point comes to lie increasingly closer to the holding point, but then the selection element moreover brushes along a very limited zone at the start of this guide flank with each movement. As the selection elements are usually made from a harder material than the presenting means, this leads to accelerated local wear of the presenting means, leading to a changed presenting position as an additional result.

If a guide flank is provided with a greater angle of inclination (an incline which is slightly greater than the incline of the selection element at this location with respect to the direction of movement), the end of the selection element will follow the inclined surface of the guide flank, so that the selection element brushes along the presenting means over a longer trajectory. This solves the problem of accelerated local wear. However, this has the drawback that the selection element is deformed further and unnecessarily during this movement, thus unnecessarily subjecting the presenting means and the stop to load. This unnecessary deformation of a large number of selection elements increases the energy consumption and the wear of parts.

This drawback is overcome by providing the selection element with a projection on the side facing the guide flanks, so that only the projection comes into contact with the first and/or the second guide flank and slides along the surface of said flank during the movement.

The above problem may present itself in any shed-forming device in which a flexibly or rotatably attached selection element is deformed or rotated by one or more guide flank(s) of a positioning element. In this case, the technical measures mentioned in the previous paragraph also offer a solution. The present patent application therefore also relates to a shed-forming device which has the feature mentioned in the above paragraph without being provided with the abovementioned features.

In this context, the term projection refers to each laterally projecting portion of the selection element. This may, for example, be a thickening, a protuberance or a bending of the material of the selection element, but an element which is attached to the selection element is also seen as a projection in the context of the present invention.

The projection keeps the selection element at a distance from the guide flank. With a guide flank which runs parallel with the direction of movement or has a small angle of inclination, the material of the selection element will consequently not only slide along the limited starting zone of this flank. The contact is formed by the projection and this projection can freely slide along the guide flank along a longer trajectory.

Preferably, the second guide flank has at least one part which is virtually parallel to the direction of the relative movement between the selection element and the presenting means. Such a guide flank makes it possible to keep the selection element in the same deformed position during part of the movement. As has been explained above, this offers the advantage that the selection element does not have to be deformed unnecessarily during the further relative movement of the presenting means and the selection element which is required to ensure engagement of the shed-forming means.

In a preferred embodiment, the selection element has an opening in the vicinity of the free end, so that an edge portion of the presenting means which extends between said contact point and the start of the guide flank is situated in said opening when the end of the selection element is in contact with a guide flank of the presenting means.

Preferably, this opening is also the hook-engagement opening for enabling the shed-forming elements to be retained. As the edge portion of the presenting means extending along the guide flank can be in the opening, the end can freely remain in contact with the selection element along a longer trajectory. This feature is preferably used in combination with the abovementioned projection, but can also be used with selection elements without such a projection. Preferably, each selection element has, at its free end, an end part which is bent at an obtuse angle and extends towards the vertical plane of the selector.

The mutual positions of the cooperating selection elements and presenting means may vary, for example due to vibrations or different dimensions or different positions during the installation of parts. The surface of the end part facing the presenting means can act as a contact area for the presenting means. As a result thereof, the presenting means will always efficiently come into contact with the selection element in order to bring the latter into the desired presenting position. In addition, the oblique contact area results in a less abrupt contact between the presenting means and the selection element. When contact takes place, the contact area of the selection element will slide along the guide surface of the presenting means, so that the impact of this first contact remains limited and the selection element is not, for example, knocked off.

In a very preferred embodiment, the shed-forming device according to the present invention comprises at least one unit which comprises at least two selection elements which extend next to one another from their free end and are connected to one another at the other end, preferably because they are configured as a single entity with a common bridge part. Such a unit can be fitted and replaced more quickly and easily than a number of separate selection elements.

The selection means and their associated presenting means are preferably also designed in such a manner that at least two groups can be distinguished, in which, viewed in the same weaving cycle, the point in time at which the selection elements of a group come into contact with their respective presenting means differs from the point in time at which the selection elements of the other group(s) come into contact with their respective presenting means.

Due to the fact that the contact between the selection elements and their presenting means no longer takes place at the same point in time for all selection elements, the noise and vibrations in machine parts caused by this contact is also spread out more over time.

Furthermore, it is preferred to provide the shed-forming device with a number of shed-forming elements with associated hook-engagement means which are provided in order to retain the shed-forming elements at a fixed height, and to provide these shed-forming elements and hook-engagement means in such a manner that at least two groups can be distinguished, in which, viewed in the same weaving cycle, the point in time at which the shed-forming elements of a group engage in their respective hook-engagement means differs from the point in time at which the shed-forming elements of the other group(s) engage in their respective hook-engagement means.

As a result thereof, the instant of contact between shed-forming elements and associated hook-engagement means is spread over time, thereby further reducing the noise pollution and the vibrations in machine parts.

The present invention furthermore also relates to a method for determining the position of elastically deformable selection elements of a shed-forming device for a weaving machine by means of electromagnetic selectors, in which each selection element can, as desired, be placed or held in an undeformed position or in a deformed position in order to determine the position of at least one warp thread, and in which, in successive weaving cycles, the undeformed selection elements are deformed under the effect of a mechanical force in the direction of an associated selector, and the selectors are actuated in order to exert a magnetic force on a number of the selection elements in order to place or keep these selection elements in the deformed position.

Such a method is known. The drawbacks of this method are identical to the abovementioned drawbacks of the known shed-forming devices. In order to overcome these drawbacks and to arrive at a very reliable and energy-saving method, the undeformed selection elements are mechanically deformed into a presenting position in which each selection element is kept at a distance from an associated selector by a stop.

As has already been mentioned above, this patent application also relates to a shed-forming device for a weaving machine which does not necessarily have the above-described features. Such a shed-forming device then comprises at least one elastically deformable or rotatably attached selection element with a free end, and a positioning means in order to bring the selection element into a deformed or rotated position, in which the positioning means and the selection element are movable with respect to one another along the longitudinal direction of the selection element, and in which the positioning means comprises at least one guide flank which is designed in such a way that the free end of the selection element comes into contact with the guide flank during said movement and follows this flank during the further movement, so that the selection element is brought or held in a deformed or rotated position.

If the positioning means is provided with a guide flank which has a small incline with respect to the direction of movement (an incline which is smaller than the incline of the selection element at said location with respect to the direction of movement) or runs parallel to this direction of movement, the selection element brushes along a very limited starting zone of this guide flank with each movement. Due to the fact that the selection elements are usually made from a harder material than the positioning means, these positioning means are subjected to accelerated local wear, leading to a different positioning as additional result.

If a guide flank with a larger angle of inclination is provided (an incline which is slightly larger than the incline of the selection element at said location with respect to the direction of movement), the end of the selection element will follow the inclined surface of the guide flank, so that the selection element brushes along the presenting means over a longer trajectory. The problem of accelerated local wear is thus solved. However, the associated drawback is that the selection element is unnecessarily deformed further during this movement. The unnecessary deformation of a large number of selection elements increases the energy consumption.

This drawback is overcome by providing the selection element with a projection on the side facing the guide flank, so that only the projection comes into contact with the guide flank during the movement and slides along the surface of said flank.

Here, the term projection refers to each laterally protruding portion of the selection element. This may, for example, comprise a thickening, a protuberance or a bending of the material of the selection element, but an element which is attached to the selection element is also regarded as a projection in the context of the present invention.

The selection element is kept at a distance from the guide flank by the projection. With a guide flank which runs parallel with the direction of movement or has a small angle of inclination, the selection element will thus not only slide along the limited starting zone of this flank. The contact is formed by the projection and this projection can freely slide along the guide flank over a longer trajectory.

The usual arrangement of a flexible selection element is such that, when it has been brought into a position to retain the shed-forming element by the selector, the selection element is more or less straight from its bending point up to the attachment point with which the shed-forming element is retained.

In addition, in an advantageous embodiment, the selection element will also be more or less parallel to the direction of movement of the shed-forming element due to the movement of the knives. More or less parallel means that, between bending point and attachment point of the selection elements, the tangent lines on these selection elements in a plane in which a point of the selection element is moved by the presenting means do not deviate by more than 20 degrees with respect to the parallel lines in the direction of movement of the shed-forming element, preferably by not more than 10 degrees and most preferably by less than 5, e.g. 0, 1 or 2 degrees.

This makes it possible to keep the flexural stress in the selection element very low and possibly reduce it to 0. In the case of an embodiment comprising a selection element which is not fixedly connected to the shed-forming element, this also ensures that the selection element does not deform to a significant extent under the action of the spring force on the shed-forming element and can, for example, also not be pulled onto the stop on the selector, as this would unnecessarily subject the stop to load. In addition, an arrangement in which the selection element is more or less parallel with the direction of movement of the shed-forming element due to the movement of the knives as has been described above, can also offer advantages for the installation space which is required for the combination of selection elements, selectors and shed-forming elements, and thus also for the compactness of the shed-forming device.

Thus, as has already been mentioned, the above-described shed-forming device does not necessarily have each of the above features, but it should however be stressed that this shed-forming device may be provided with one or more of these features, and then obviously obtains the abovementioned effects and advantages as a result.

Preferably, the positioning means comprises a first and a second guide flank which are designed in such a manner that, during said movement, the free end of the selection element first comes into contact with the first guide flank and follows said flank, so that the free end is pushed in a sideward direction and the selection element is brought into a deformed or rotated position, and that, during the further movement, the free end of the selection element then comes into contact with the second guide flank and follows said second guide flank so that the selection element is first deformed or rotated further and is then held in virtually the same deformed or rotated position during the further movement.

At least a part of the second guide flank is preferably virtually parallel with the direction of the relative movement between the selection element and the positioning means. Such a guide flank allows the selection element to be kept in the same deformed or rotated position during part of the movement, so that the parts are not unnecessarily subjected to load and unnecessary energy consumption is prevented.

In a preferred embodiment, the selection element comprises an opening in the vicinity of the end part which is designed such that, when the projection on the selection element is in contact with a guide flank of the presenting means, an edge portion of the presenting means which extends between this contact point and the start of the guide flank is situated in said opening.

At the free end, the selection element may comprise an end part which is bent at an obtuse angle and directed away from the guide flanks.

The positions of the cooperating selection elements and positioning means with respect to one another may vary, for example due to vibrations or different dimensions or different positions during installation of parts. The surface of the end part facing the presenting means can serve as a contact area for the presenting means. As a result thereof, the presenting means will always come into contact with the selection element in an efficient manner in order to bring the latter into the desired deformed or rotated position. In addition, the oblique contact area results in a less abrupt contact between the presenting means and the selection element. When contact takes place, the contact area of the selection element will slide along the guide surface of the presenting means, so that the impact of this first contact remains limited and the selection element is not, for example, knocked off.

The selection element may be provided with a hook-engagement opening into which a projection of a shed-forming element or of a fixedly arranged part can engage. However, the reverse situation in which the selection element comprises a projection which is designed to engage in a hook-engagement opening of a shed-forming element or of a fixedly arranged part is also possible. Said projection is preferably hook-shaped.

The abovementioned guide flanks may also be provided on the selection element. The presenting means then comprises, for example, a straight flank by means of which it makes contact with the guide flank on the selection element. During the movement of the presenting means and the selection element with respect to one another, the selection element will be pushed in a lateral direction and deformed in this embodiment as well.

In the following description, some preferred embodiments and parts of a shed-forming device according to the invention will be described in more detail. The sole intention of this detailed description is to indicate how the invention can be achieved and to illustrate and, where necessary, explain the operation and the particular features thereof. This description can therefore not be regarded as a limitation of the scope of protection of this patent and neither can the area of application of the invention be limited on the basis of this description.

BRIEF DESCRIPTION OF THE DRAWINGS

In this description, reference is made to the attached figures, in which

FIGS. 1 to 6 diagrammatically show a flexible holding element together with an electromagnetic selector and a hook with presenting means, in which FIGS. 1 to 4 show the successive phases during presentation of the holding element by means of the upwardly moving hook, FIG. 5 shows the situation in which the hook is retained at a fixed height by the selection element, and FIG. 6 shows the situation in which the hook is not retained at a fixed height;

FIGS. 13, 14 and 15 in each case diagrammatically show the same four selection elements together with a respective selector and a hook with presenting means, these figures representing three successive phases during the presentation of the selection elements;

FIGS. 16 to 19 show diagrammatic representations of a flexible holding element together with an electromagnetic selector and a hook with presenting means, the figures only differing from one another by the fact that the stop is provided at another location on the selector;

FIGS. 20 and 21 show diagrammatic representations of a selection element which forms part of an up and down moving hook together with an electromagnetic selector and an engagement means, the stop being provided on the selector (FIG. 20) or on the selection element (FIG. 21), respectively;

FIGS. 22 and 23 show a diagrammatic representation of a fixedly secured flexible holding element together with an electromagnetic selector and a up and down moving hook, the stop being provided on the selector (FIG. 22) or on the selection element (FIG. 23), respectively;

FIGS. 25, 26 and 27 show a perspective view, a front view and a side view, respectively, of a unit with six selection elements;

FIG. 28 shows a detail view of the circled portion of the selection elements on the side view from FIG. 27;

DETAILED DESCRIPTION OF EMBODIMENTS

Figure 5:
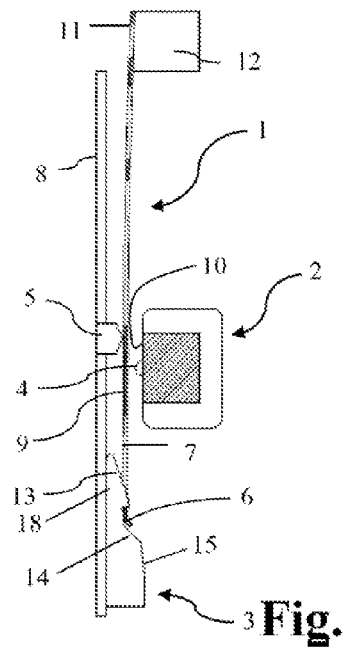
Figure 6:
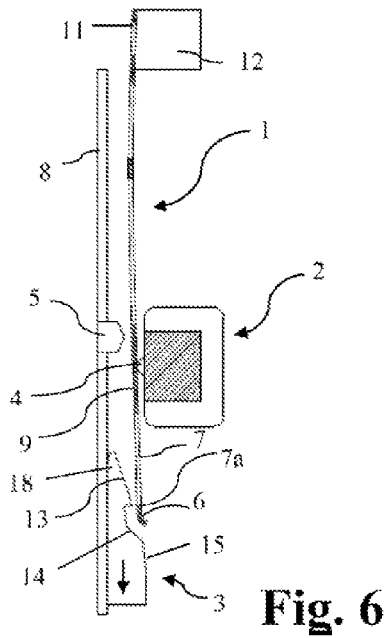
Figure 7:
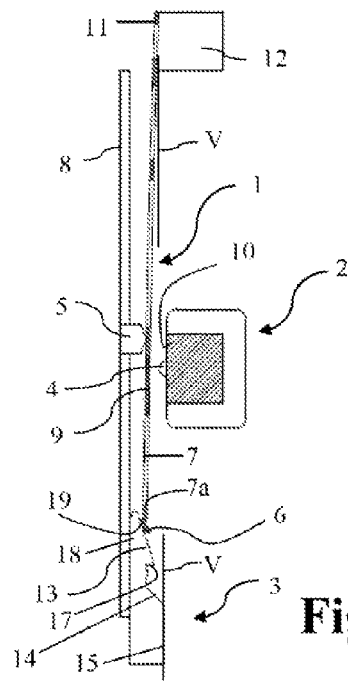
FIGS. 7 to 12 show the same as FIGS. 1 to 6, the only difference being that the end of the holding element is now provided with a projection which makes contact with the guide flanks of the hook.
Figure 8:
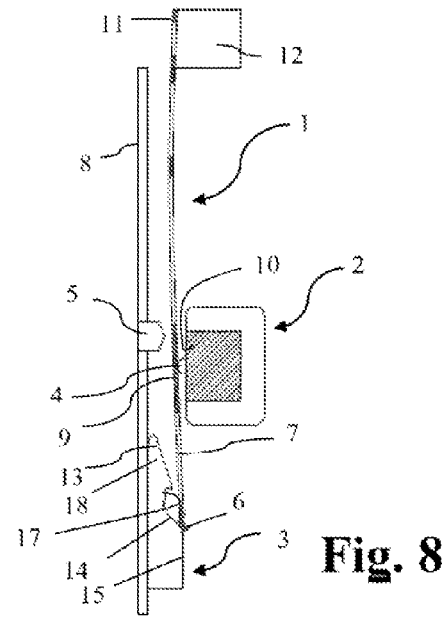
Figure 9:
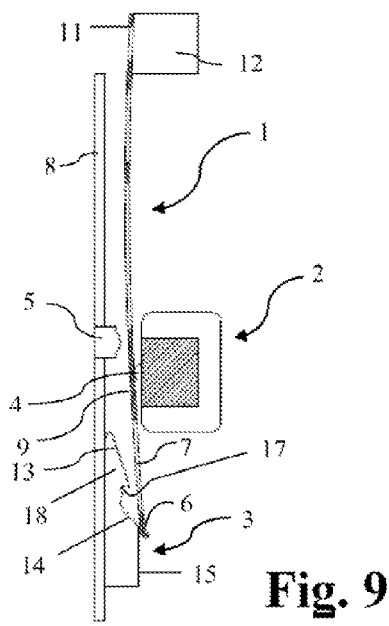

In the arrangements which are diagrammatically shown in FIGS. 1 to 19, the selection element (1) is in each case designed as a thin strip consisting of flexible and elastically deformable material, the upper end (11) of which is attached to a fixed part (12) of the shed-forming device. This selection element (1) is attached in such a manner that it extends to the left of the vertical direction (V) at a small angle. On the left-hand side of the selection element, there is a fixed supporting element (5). If no forces are exerted on the selection element (1), the selection element (1) is forced against this fixed supporting element (5) due to its elasticity, as a result of which it is under a slight prestress which counteracts a deformation to the right. The supporting element (5) ensures that the position of the selection element (1) with respect to the other parts, in particular the presenting means (3), is guaranteed.

At its free end, the selection element (1) has an end part (6) which is bent to the right at an obtuse angle, and has a hook-engagement opening (7) in the vicinity of this end part into which the head portion (18) of a hook (3) can engage.

The hook (3), only the upper end of which is illustrated, cooperates with known shed-forming means (not shown in the figures) so as to position one or more warp threads in each weaving cycle with respect to the level at which pick threads are introduced in a weaving machine. To this end, the hook (3) is caught by a up and down moving knife (not shown) and at the same time held in its vertical movement path by guide means (8).

Above the hook-engagement opening (7), the selection element (1) has a closed part (9) made of magnetically influenceable material which is situated opposite the force-exerting pole surfaces (10) of an electromagnetic selector (2). The electromagnetic parts of the selector (2) are illustrated diagrammatically in the figures by a hatched rectangle, so that the force-exerting pole surfaces (10) are diagrammatically represented in the drawings by the left-hand vertical side of this rectangle. The zone in which the pole surfaces are situated, also referred to as the pole zone, is the zone which extends between the edges of the pole surface or of the plurality of pole surfaces which are furthest apart. The space between the two parallel transverse planes (A),(B) which coincide with these edges which are furthest apart is the space in which the stop (4) is preferably provided. The intermediate distance between these transverse planes (A, B) denoted in FIG. 1 with the letter w.

In the figures, except for FIGS. 16 to 19, the stop (4) is arranged centrally in the pole zone, in the central part between the boundary surfaces (C, D) with an intermediate distance (w/2) which is half the intermediate distance (w) between the abovementioned transverse planes (A, B). The intermediate distance between the transverse planes (A,B) and the closest boundary surfaces is then approximately equal to an intermediate distance w/4.

The stop (4) is provided on the selector (2) in the embodiments from FIGS. 1 to 19, 20, 22, 24, 29 and 30. In the embodiments according to FIGS. 21 and 23, the stop is provided on the selection element (1). In each case, the stop (4) is provided with a contact area which has a convex shape in a vertical cross section.

The upper portion of the hook (3) is provided with guide flanks (13),(14),(15) to push the selection element (1) towards the selector (2), in other words to present it, during its upward movement. Thus, the hook (3) here serves as a presenting means. The upper portion of the hook (3) is also provided with a recess (16) which is limited at the top by a hook-shaped edge (17). As is explained further with reference to FIG. 5, it is this hook-shaped edge (17) with which the hook (3) will rest on the bottom edge (7a) of the hook-engagement opening (7) of the selection element (1) when it engages in the hook-engagement opening (7).

During the upward movement of the hook (3), the front guide flank (13) thereof strikes against the end part (6) on the free end of the selection element (1). The instant at which contact is made, is illustrated in FIG. 1. As the hook (3) is moved upwards further, the end part (6) slides further along this guide flank (13), as a result of which the end part (6) is pushed towards the selector (2) and the selection element (1) is deformed.

During the further upward movement of the hook (3) (see FIG. 2), the end part (6) beyond the recess (16) comes into contact with the second guide flank (14, 15). A first part (15) of this second guide flank—the part which delimits the recess (16) at the bottom—pushes the selection element (1) further towards the selector (2), as a result of which the selection element is deformed further. This further deformation beyond the first contact with the stop (4) is carried out in order to ensure that all selection elements (1) are brought into the presenting position in which they bear against a respective stop (4). This so-called 'overpresenting' is illustrated more clearly with reference to FIGS. 13 to 15.

During the further upward movement of the hook (3), the bottom end part (6) of the selection element (1) comes into contact with the second part (15) of the second guide flank (14, 15), as is illustrated in FIG. 3. The further upward movement of the hook (3) is necessary in order to bring the hook into a position in which its head portion (18) is brought sufficiently far beyond the bottom edge (7a) of the hook-engagement opening (7) of the selection element (1) in order to ensure that this head portion (18) readily enters the hook-engagement opening (7) at the start of the downward movement of the hook (3) when the associated selection element (1) is not attracted by the selector and springs back. The head portion (18) is the portion from the top end of the hook which is delimited by the hook-shaped edge (17) at the bottom, and which, in side view, has a virtually triangular shape.

The second portion (15) of the second guide flank (14, 15) is inclined with respect to the vertical direction (V). This angle of inclination has to be greater than the incline of the selection element (1) in this location, so that the bottom end part (6) of the selection element (1) can freely follow the inclined guide surface (15) until it reaches the position which is shown in FIG. 4. This causes a further deformation of the selection element (1), until the hook has reached its outermost point, as imposed by the movement of the knives.

The selector (2) is actuated in order to optionally attract the selection element (1). An electrical current is passed through the selector coil in order to attract the selection element (1) and hold it in a position against the stop (4). This excitation of the selector coil can already start before the presentation and overpresentation have ended.

If the selection element (1) is not attracted by the selector (2) (see FIG. 5), it springs back to the position from FIG. 1 when the hook moves back down. In this case, the head portion (18) of the hook (3) ends up in the hook-engagement opening (7) of the selection element. As the hook (3) is moved further down, it ultimately reaches the position from FIG. 5, in which the hook-shaped edge (17) rests on the bottom edge (7a) of the hook-engagement opening (7).

However, if the selection element (1) is attracted (see FIG. 6), the hook (3) is not able to engage in the hook-engagement opening (7) of the selection element (1) during its downward movement, so that it follows the knife moving downward. If a hook does engage in the hook-engagement opening, it will partially follow the above cycle, after the downward movement and in the movement back up of the associated knife. The associated knife will catch the hook, so that it moves further upwards, beyond the engagement point of the selection element, as a result of which the latter beyond the recess finally comes in contact with the first part (14) of the second guide flank (14, 15), with a path and associated selection options as already described above for a hook which has followed the entire movement of the knife.

According to the present invention, an embodiment has also been developed which prevents the unnecessary further deformation of the second guide flank (14, 15) by the second part (15). This is illustrated by means of FIGS. 7 to 12 which show the same situations as FIGS. 1 to 6.

In order to prevent the additional deformation of the guide flank by the second part (15), this flank part (15) has to run virtually parallel with the direction of movement (V) of the hook (3).

In order to ensure that the end part (6) of the selection element (1) can slide along this flank part (15) during the entire trajectory of the further movement, a projection (19) facing the guide flank (14, 15) is provided on the end part (6) of the selection element (1). The projection (19) is formed by bending the selection element (1), towards the free end, away from the selector and making the last end portion run back obliquely to the selector (2). The projection is formed by the material facing the guide flanks (13), (14, 15) in the bend which is thus formed.

Figure 10:
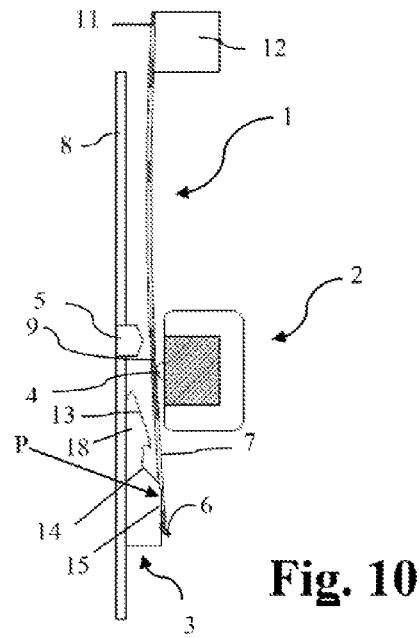
Figure 11:
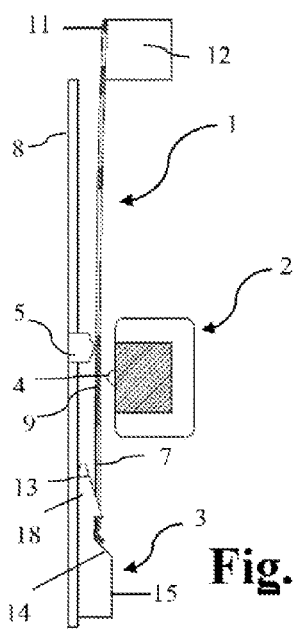
Figure 12:
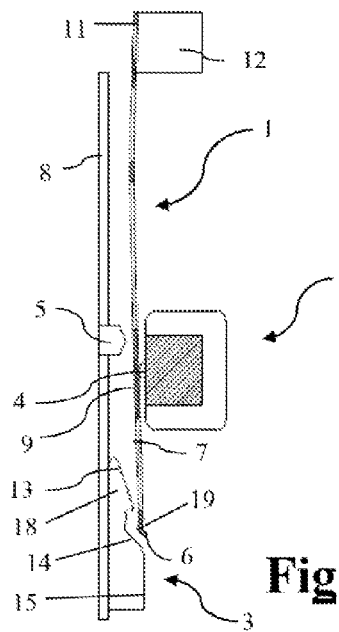

In FIG. 10, an arrow (P) indicates the location where an edge portion of the hook (3) extending along the flank (15) is situated in the hook-engagement opening (7) of the selection element (1) when the end part (6) provided with the projection (19) slides along this guide flank (15). In order to prevent a decrease or wear of the material, the location, the shape and the size of the hook-engagement opening (7) have been determined in such a manner that the edges of the opening (7) cannot come into contact with the material of the hook (3) at any point in time.

Figure 13:
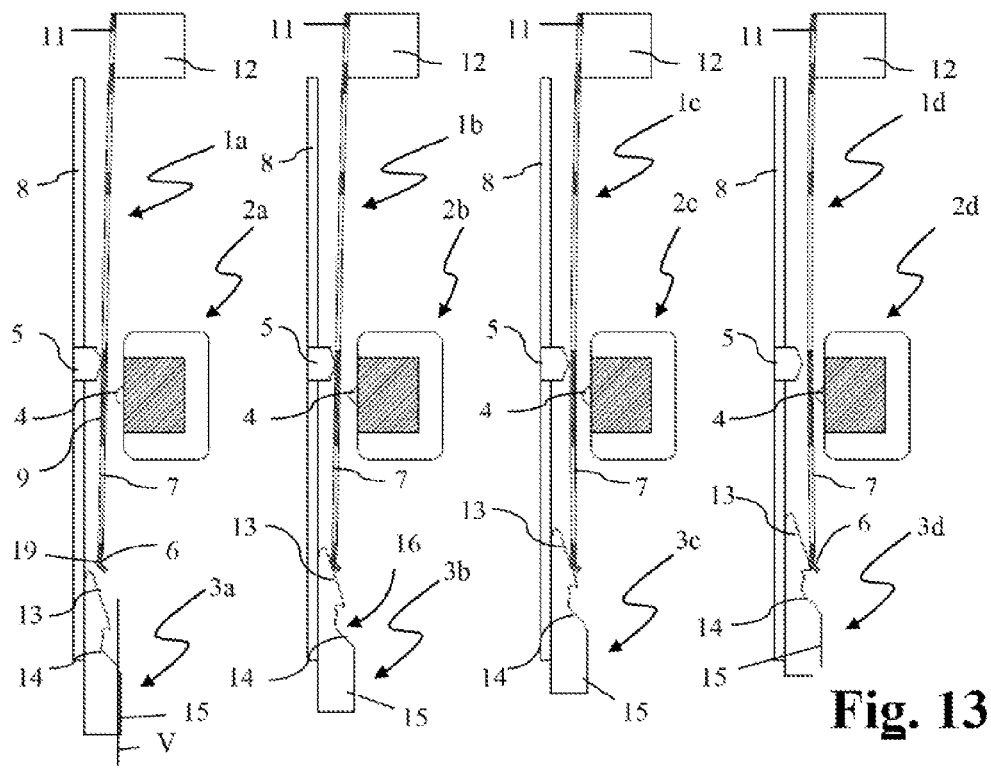
Figure 14:
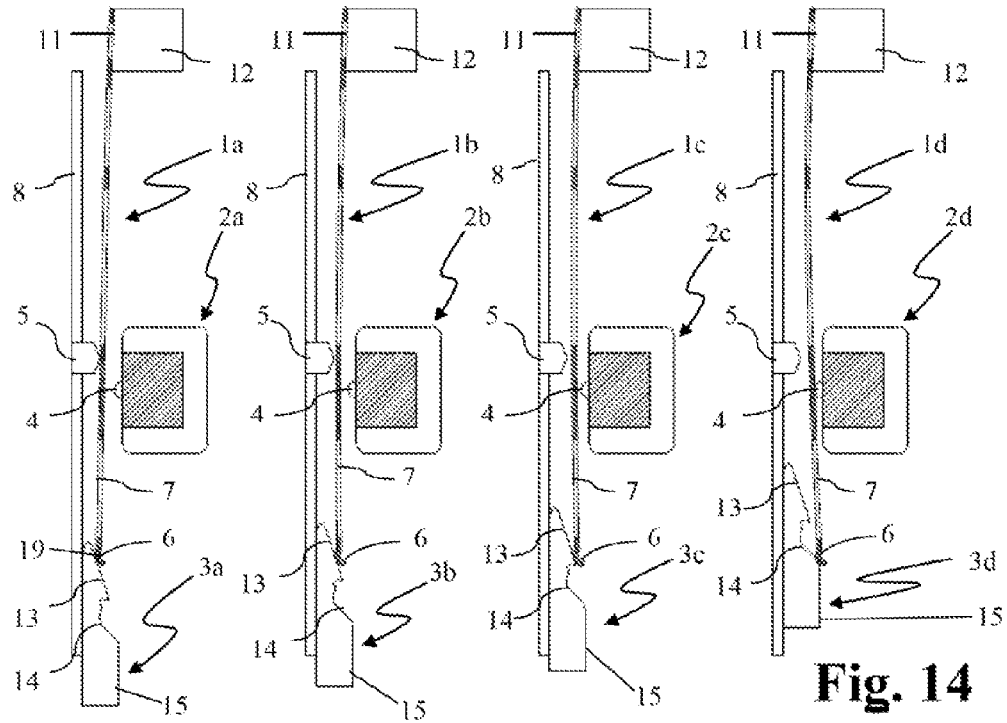

FIGS. 13 to 15 in each case show four selection elements (1*a*), (1*b*), (1*c*), (1*d*) which are arranged at a fixed height and belong to the same shed-forming device at the same point in time together with a respective selector (2*a*), (2*b*), (2*c*), (2*d*) and a respective hook (3*a*), (3*b*), (3*c*), (3*d*) with guide flanks (13, 14, 15).

In each of FIGS. 13, 14 and 15, these four selection elements (1*a*), (1*b*), (1*c*), (1*d*) are shown at a different (subsequent) point in time during the movement. However, as a result of mutual differences in positioning, dimensions, actions of forces, etc., the selection elements (1*a*), (1*b*), (1*c*), (1*d*) are not in the same position with respect to the guide flanks (13, 14, 15) at the same point in time during the movement and are therefore also not in the same position with respect to the stop (4). Thus, the selection element (1*a*) which is furthest to the left is not yet in contact with the hook (3*a*) at the point in time of FIG. 13, whereas the other three selection elements (1*b*), (1*c*), (1*d*) of FIG. 13 are in contact with the hook (3*a*) at that point in time.

Thus, it can also be seen that the selection element (1*d*) which is furthest to the right is already in contact with the stop (4) at the point in time of FIG. 14, whereas this is not yet the case for the other selection elements (1*a*), (1*b*), (1*c*) at that point in time.

All selection elements are deformed further by the guide flanks (13), (14) during the further movement after the point in time shown in FIG. 14 until they have all been brought against their respective stop (4) at the point in time shown in FIG. 15. As the selection element (1*d*) which is furthest to the right at the point in time shown in FIG. 14 was already in contact with the stop (4), this selection element (1) is overpresented during its further displacement by the first part (14) of the second guide flank (14, 15).

Since the second part (15) of this second guide flank (14, 15) runs parallel with the direction of movement (V), the selection elements (1*a*), (1*b*), (1*c*), (1*d*) are not deformed further by this flank part (15).

In FIGS. 16 to 19, with the above-described embodiment of a fixedly secured selection element (1) together with an electromagnetic selector (2) and a hook (3) with guide surfaces (13, 14, 15), the stop (4) is provided at different positions on the selector. In the embodiment illustrated in FIG. 16, the stop (4) is situated in a central position between the transverse planes (A), (B) which delimit the zone of the pole surfaces (10). In FIGS. 17 and 18, this is a position near the top (A) and the bottom transverse plane (B), respectively, while FIG. 19 shows that this position may also be situated outside the space between said transverse planes (A), (B).

In FIGS. 20 and 21, a selection element (1) is shown which is the upper portion of a hook which can be moved up and down by a knife (not shown) between guide means (36), (37), together with an electromagnetic selector (2) and an engagement means (21) arranged at a fixed height. In FIG. 20, the stop (4) is provided on the selector, whereas in FIG. 21, the stop (4) is provided on the selection element (1).

The selection element (1) has a hook-engagement opening (23), while the engagement means (21) comprises a hook-shaped projection (22). The selection element (1) can be pushed in the direction of the selector (2) and into a presenting position by means of presenting means (not shown). In the case of FIG. 20, the selection element (1) bears against the stop (4). In the case of FIG. 21, the stop (4) of the selection element bears against the selector (2). In both cases, the hook-shaped projection (22) is situated in the hook-engagement opening (23).

A selection element (1) which is attracted by the selector (2) will hook onto the hook-shaped projection (22) during its downward movement. A selection element (1) which is not attracted by the selector (2), will spring back into its original position in which the hook-shaped projection (22) is no longer situated in the hook-engagement opening (23) and will move concomitantly with the knife (not shown) during its downward movement.

FIGS. 22 and 23 show a selection element (1) which is arranged at a fixed height, together with a up and down moving hook (3) and an electromagnetic selector (2). In the embodiment from FIG. 22, the stop (4) is provided on the selector (2), whereas in the embodiment from FIG. 23, the stop (4) is provided on the selection element (1). The selection element (1) has a hook-engagement opening (7), while the hook (3) comprises a hook-shaped head (24). The selection element (1) can be pushed in the direction of the selector (2) and into a presenting position by presenting means (not shown). In the case of FIG. 22, the selection element (1) then bears against the stop (4). In the case of FIG. 23, the stop (4) of the selection element then bears against the selector (2). In both cases, the hook-shaped head (24) is then not in the hook-engagement opening (7).

If the selection element (1) has been attracted by the selector (2), the hook (3) will not be able to engage in the hook-engagement opening (7) and be carried along by the knife during its downward movement. If the selection element (1) is not attracted by the selector (2), it will spring back to a position in which the hook-shaped projection (24) is situated in the hook-engagement opening (7). During the downward movement of the knife (not shown), the hook-shaped head (24) will engage in the hook-engagement opening (7) and the hook (3) will be held at a fixed height. In this case, the hook-shaped head (24) rests on the bottom edge (7*a*) of the hook-engagement opening (7).

Figure 24:
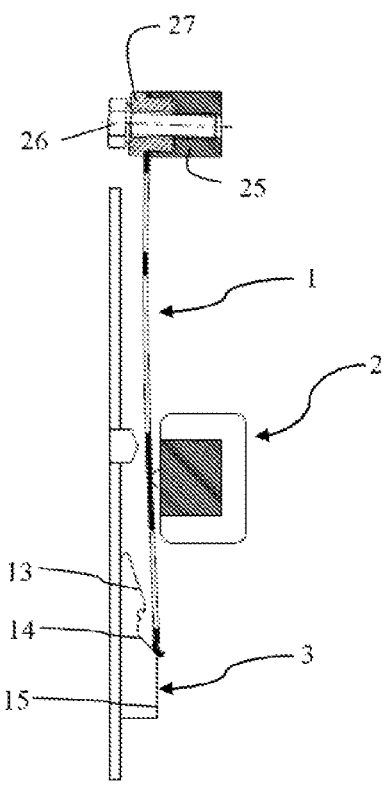
FIG. 24 shows a diagrammatic representation of a fixedly secured flexible holding element together with an electromagnetic selector and a up and down moving hook with presenting means, the holding element being connected to a chassis part of the shed-forming device.
Figure 25:
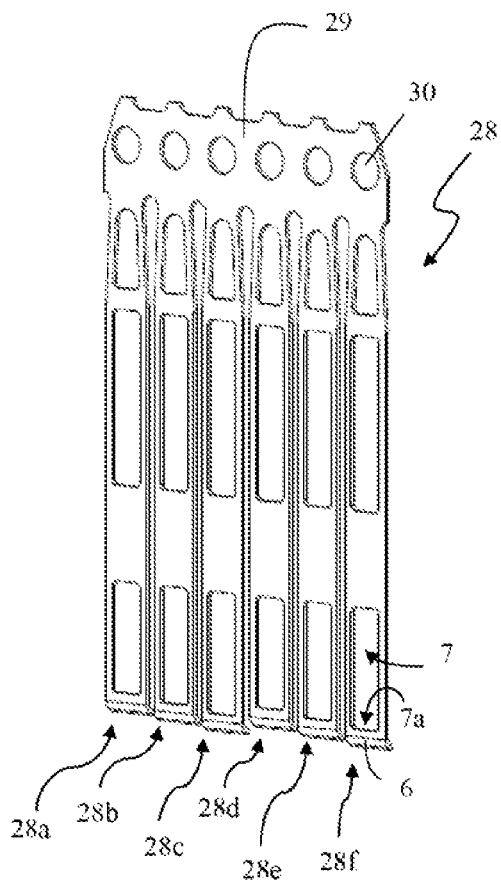

FIG. 24 shows a selection element (1) together with an electromagnetic selector (2) and a up and down moving hook (3) with guide flanks (13), (14, 15), as has been described above with reference to FIGS. 1 to 12. The selection element (1) of the embodiment from FIG. 24 is attached to a fixing element (25) which is attached to the chassis (27) of the jacquard machine by means of a bolt (26). The forces which are exerted on the hooks (3) by the warp threads and the retracting springs are transferred to a chassis part (27) via the selection elements (1) and not to the selector (2) or another part of the selection device.

It is possible to provide units (28) comprising more selection elements (28a-28f) in the shed-forming device according to the present invention. Thus, it is possible to produce a number of adjacent selection elements from the same piece of sheet-shaped material. Such a single-part component (28) with six selection elements (28a), (28b), (28c), (28d), (28e), (28f) is illustrated in FIGS. 25 to 28.

The six selection elements are made in three different lengths, so that the selection elements can come into contact with their respective presenting means at different points in time during the same weaving cycle. Spreading this instant of contact over time reduces noise pollution and vibrations in the parts of the device.

For the different selection elements (28a)-(28f) of a unit, the respective bottom edges (7a) of the hook-engagement openings (7) are also provided on three different levels. As a result thereof, the hooks associated with these selection elements will engage in these hook-engagement openings (7) at different points in time during the same weaving cycle. The contact between the hook-shaped edges or projections of the hooks and the bottom edges (7a) of the hook-engagement openings (7) is thus also spread over time, further reducing noise pollution and vibrations.

Two series of selection elements (28a-28c), (28d-28f) are provided next to one another, each series successively comprising a first selection element (28a), (28d) whose length is shortest and whose edge (7a) is at the highest level, a second selection element (28b), (28e) which is slightly longer and whose edge (7a) is situated lower compared to that of the first selection element, and a third selection element (28c), (28f) which is longer still and whose edge (7a) is situated lower compared to the second selection element. In FIGS. 27 and 28, the three different lengths can be seen most clearly.

Each unit (28) consists of six selection elements (28a)-(28f) which are adjacent to one another in the same plane and which have a common bridge part (29) at their upper end so that they form a single entity. Openings (30) are provided in this bridge part (29) at their upper end for attaching the unit (28) to a fixed part of the shed-forming device.

Five different zones (a-e) can be distinguished on the selection elements (1):
a stiff zone (a) in the vicinity of the end which has to be fixedly attached, in this case the bridge part (29);
a first flexible zone (b) which has a lower stiffness than the stiff zone (a), and whose flexibility determines the speed of response of the selection element when actuating the associated selector in order to bring the selection element in the deformed or the undeformed position;
a magnetically influenceable zone (c) with a greater stiffness than the first flexible zone (b);
a second flexible zone (d) which is situated beyond the magnetically influenceable zone (c), and which has a lower stiffness than the magnetically influenceable zone (c), and whose flexibility determines the amount of energy which is required to deform a selection element (28a)-(28f) bearing against a stop (4) further in the direction of the selector (2); and
an end zone (e) on the free end where an end part (6) which is bent at an obtuse angle forms a contact area for the presenting means.

Figure 29:
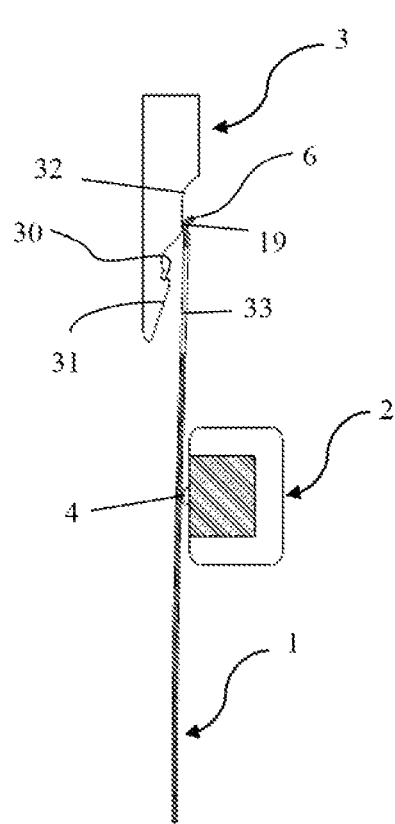
FIGS. 29 and 30 show a diagrammatic representation of a selection element which forms part of a up and down moving hook together with an electromagnetic selector and engagement and presenting means which are designed as a single piece (FIG. 29) and as separate parts (FIG. 30), respectively.
Figure 30:
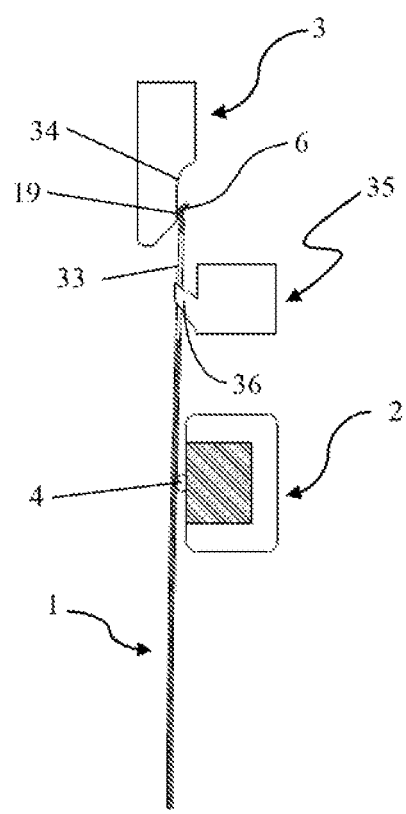

The embodiment illustrated in FIGS. 29 and 30 comprises a flexible and elastically deformable selection element (1) which forms the upper portion of a up and down moving hook together with an electromagnetic selector (2) and engagement and presenting means provided at a fixed height. In the embodiment from FIG. 29, the presenting means (3) are arranged at a fixed height and the hook-engagement means are incorporated in the same part (3). A hook-shaped edge (30) acts as engagement means, while the guide flanks (31), (32) ensure presentation of the selection element (1). The selection element (1) comprises a hook-engagement opening (33) and an upper free end which is provided with a projection (19) which is directed towards the guide flanks (31), (32) and an end part (6) which is bent at an obtuse angle and is directed obliquely, away from these guide flanks (31), (32).

If the selection element (1) is attracted by the selector (2), it cannot hook onto the hook-shaped edge (30) by means of the hook-engagement opening (33) and the hook moves concomitantly with the downwardly moving knife. If the selection element (1) is not attracted by the selector (2), then it can hook onto this edge (30).

In the embodiment according to FIG. 30, the fixedly secured presenting means (3) has a continuous guide flank (34) and does not comprise any hook-engagement means, since the hook-engagement means, in the form of a hook-shaped projection (36), are provided on a separate part (35) which is also arranged at a fixed height.

When the selection element (1) is attracted, the selection element will engage in the hook-shaped projection (36) by means of the hook-engagement opening (33), so that the hook is held at a fixed height. If the selection element (1) is not attracted, it will not engage in the projection (36) and will move concomitantly with the downwardly moving knife.

The invention claimed is:

1. Shed-forming device for a weaving machine, comprising:
   at least one elastically deformable or rotatably attached selector with a free end, and
   a positioner to bring the selector into a deformed or rotated position,
   wherein the positioner and the selector are movable with respect to one another along the longitudinal direction of the selector, and
   wherein the positioner comprises at least one guide flank which is designed in such a way that the free end of the selector comes into contact with the guide flank during said movement and follows this flank during the further movement, so that the selector is brought or held in a deformed or rotated position,
   wherein the selector comprises a projection on the side facing the at least one guide flank, so that only the projection comes into contact with the guide flank during the movement and slides alone the surface of said flank.

2. Shed-forming device for a weaving machine according to claim 1, characterized in that the positioner comprises a first and a second guide flank which are designed in such a manner that, during said movement, the free end of the selection element first comes into contact with the first guide flank and follows said flank, so that the free end is pushed in a sideward direction and the selector is brought into a deformed or rotated position, and that, during the further movement, the free end of the selector then comes into contact with the second guide flank and follows said second guide flank so that the selector is first deformed or rotated further and is then held in virtually the same deformed or rotated position during the further movement.

3. Shed-forming device for a weaving machine according to claim 2, characterized in that at least a part of the second guide flank is virtually parallel with the direction of the relative movement between the selector and the positioner.

4. Shed-forming device for a weaving machine according to claim 1, characterized in that the selector comprises an opening in the vicinity of the end part which is designed such that, when the projection on the selector is in contact with a guide flank of the positioner, an edge portion of the positioner which extends between said contact point and the start of the guide flank is situated in said opening.

5. Shed-forming device for a weaving machine according to claim 1, characterized in that, at the free end, the selector comprises an end part which is bent at an obtuse angle and directed away from the guide flanks.

\* \* \* \* \*